United States Patent
Motai et al.

(10) Patent No.: US 8,545,394 B2
(45) Date of Patent: Oct. 1, 2013

(54) SELECTIVE CANNULATION METHOD FOR LUMINAL TISSUE HAVING BRANCH SECTION

(75) Inventors: Kosuke Motai, Tokyo (JP); Ayano Ishioka, Tokyo (JP)

(73) Assignee: Olympus Medical Systems Corp. (JP)

( * ) Notice: Subject to any disclaimer, the term of this patent is extended or adjusted under 35 U.S.C. 154(b) by 1017 days.

(21) Appl. No.: 12/354,188

(22) Filed: Jan. 15, 2009

(65) Prior Publication Data
US 2010/0179383 A1 Jul. 15, 2010

(51) Int. Cl.
A61B 1/00 (2006.01)
A61B 1/04 (2006.01)

(52) U.S. Cl.
USPC ............ 600/104; 600/107; 600/114; 600/139

(58) Field of Classification Search
USPC ................ 600/104, 107, 139, 106, 114, 585, 600/593
See application file for complete search history.

(56) References Cited

U.S. PATENT DOCUMENTS

| 7,232,434 B2 | 6/2007 | Suyama et al. | 604/528 |
| 2003/0078473 A1* | 4/2003 | Richardson | 600/115 |
| 2004/0186349 A1* | 9/2004 | Ewers et al. | 600/114 |
| 2006/0135963 A1* | 6/2006 | Kick et al. | 606/108 |
| 2007/0265595 A1* | 11/2007 | Miyamoto et al. | 604/528 |

FOREIGN PATENT DOCUMENTS

| JP | 05-168715 | 7/1993 |
| JP | 05-184528 | 7/1993 |
| JP | H7-148171 | 6/1995 |
| JP | 2001-017386 | 1/2001 |
| JP | 2001-231852 | 8/2001 |
| JP | 2002-0272675 | 9/2002 |
| JP | 2008-526360 | 7/2008 |
| WO | WO 2006/073725 | 7/2006 |

OTHER PUBLICATIONS

Office Action issued by the Japanese Patent Office on Dec. 7, 2010 in connection with corresponding Japanese Patent Application No. 2010-506756.
English translation of Japanese Office Action issued in connection with Japanese Patent Application No. 2010-506756 on Dec. 7, 2010.
Office Action issued by the Japanese Patent Office on Sep. 7, 2010 in connection with corresponding Japanese Patent Application No. 2010-506756.
English translation of Japanese Office Action issued in connection with Japanese Patent Application No. 2010-506756 on Sep. 7, 2010.

* cited by examiner

Primary Examiner — Alireza Nia
(74) Attorney, Agent, or Firm — Ostrolenk Faber LLP

(57) ABSTRACT

A selective cannulation method for a lumenal tissue's branch section includes: a first step for guiding an endoscope having a channel to an aperture section of the lumenal tissue; a second step for inserting a distal end of an endoscopic treatment instrument through the channel into the aperture section of the lumenal tissue; a third step for having the distal end of the endoscopic treatment instrument make contact with a pipe wall extending from the aperture section of the lumenal tissue to the branch section at two opposed points on the pipe wall by deforming the distal end of the endoscopic treatment instrument; a fourth step for sliding and moving the distal end of the endoscopic treatment instrument to the branch section while having the distal end of the endoscopic treatment instrument make contact with the pipe wall; and a fifth step for inserting the distal end of the endoscopic treatment instrument into a predetermined branch lumen divided from the branch section.

6 Claims, 20 Drawing Sheets

SELECTIVE CANNULATION METHOD FOR LUMINAL TISSUE HAVING BRANCH SECTION

BACKGROUND OF THE INVENTION

1. Field of the Invention

The present invention relates to a selective cannulation method conducted to a branch section or a collecting section of a lumenal tissue of a living organ, and relates to an endoscopic treatment instrument for use in the aforementioned method.

2. Background Art

Endoscopic retrograde cholangiopancreatography (ERCP) is a conventionally-known diagnostic method for acknowledging in abnormality in a pancreas, a cholecyst, or a bile duct. The ERCP provides X-ray photography by inserting a catheter into the duodenal papilla and subsequently injecting contrast agent directly into a pancreatic duct or a bile duct (see, for example, Japanese Unexamined Patent Application, First Publication No. 2002-272675). In addition, selective insertion of a catheter or an endoscopic treatment instrument is conducted via a duodenal papilla for removing gallstones or for indwelling a stent into a constricture developed in a bile duct. Reliable insertion of endoscopic treatment instruments or the like into the bile duct requires skill since the bile duct and a pancreatic duct have apertures on a common duct through which they communicate with a duodenal papilla.

SUMMARY OF THE INVENTION

A first aspect of the present invention is a selective cannulation method for a luminal tissue's branch section, the method comprising: a first step of guiding an endoscope having a channel to an aperture section of the luminal tissue; a second step of inserting a distal end of an endoscopic treatment instrument through the channel into the aperture section; a third step of having the distal end of the endoscopic treatment instrument make contact with a pipe wall extending from the aperture section of the luminal tissue to the branch section at two opposed points on the pipe wall by deforming the distal end of the endoscopic treatment instrument; a fourth step of sliding and moving the distal end of the endoscopic treatment instrument to the branch section while having the distal end of the endoscopic treatment instrument make contact with the pipe wall; and a fifth step of inserting the distal end of the endoscopic treatment instrument into a predetermined branch lumen divided from the branch section.

PREFERRED EMBODIMENTS

A first embodiment of an endoscopic treatment instrument according to the present invention will be explained as follows with reference to FIGS. 1 to 22.

Figure 1:
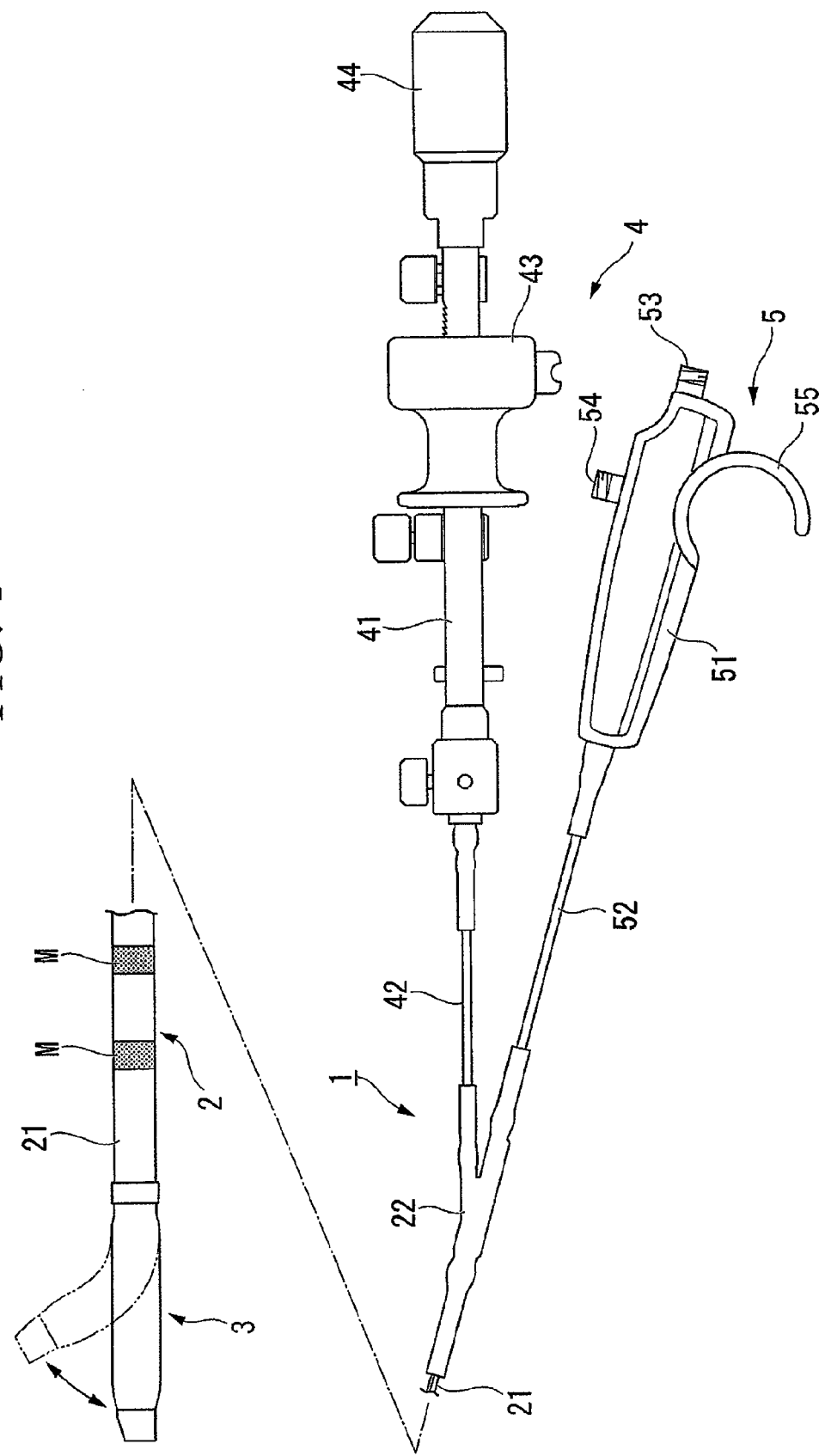
FIG. 1 shows an endoscopic treatment instrument according to a first embodiment of the present invention.

FIG. 1 shows the external view of an endoscopic treatment instrument 1 according to the present embodiment. As shown in FIG. 1, the endoscopic treatment instrument 1 has an elongated insertion section 2 extending in the axial line direction. The insertion section 2 has a tube 21, and a bending-movement section 3 capable of bending is connected to the distal end of the tube 21. In should be noted that, the distal end of the tube 21 is enlarged in FIG. 1 for better understanding of the configuration of the bending-movement section 3.

A connector 22 is connected to the proximal end of the tube 21. The connector 22 has a first operating section 4 laterally branching from the axial line of the tube 21; and a second operating section 5 disposed in the axial line direction of the tube 21.

Provided on the first operating section 4 are: a connection pipe 42 having one of its two ends connected to the connector 22; a first operating unit 41 connected to the other end of the connection pipe 42; a grip 44 fixed on the proximal end of the first operating unit 41; and a slider 43 provided to be extendable or retractable in the axial line direction of the first operating unit 41.

Provided on the second operating section 5 are: a connection pipe 52 having one of its two ends connected to the connector 22; a second operating unit 51 connected to the other end of the connection pipe 52; a first aperture 53 having an aperture directed in the axial line direction of the connection pipe 52 in the vicinity of the proximal end of the second operating unit 51; and a second aperture 54 having an aperture on the outer surface of the second operating unit 51. In addition, a substantial C-letter shaped flexible hook 55 is provided on the second operating unit 51. The hook 55 serves as a hook for locking the second operating unit 51 at an arbitrary position on the outer surface of the endoscope.

Figure 2A:
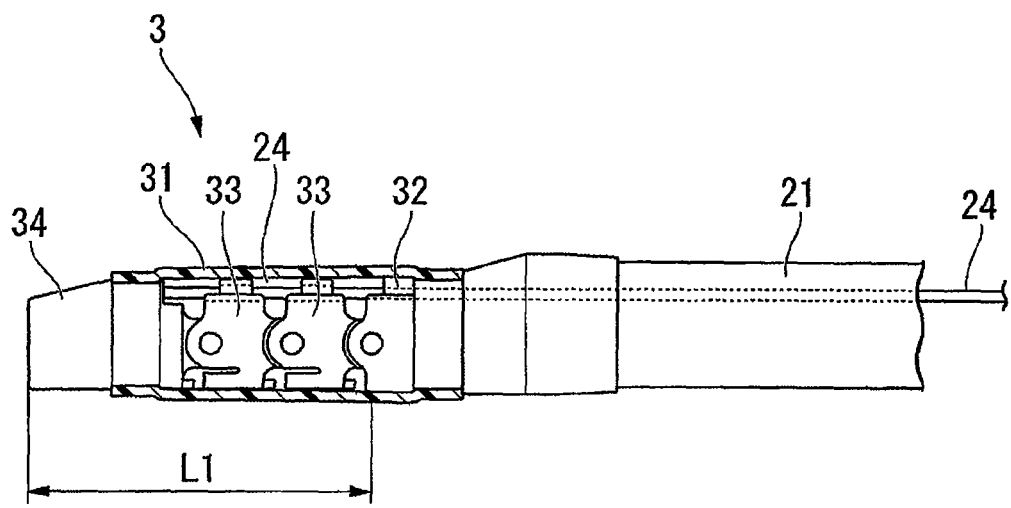
FIG. 2A is an enlarged cross sectional view showing a distal end section of the treatment instrument.

FIG. 2A is an enlarged view showing the distal end of the endoscopic treatment instrument 1 partially in cross-section. As shown in FIG. 2A, the bending-movement section 3 provided onto the distal end of the tube 21 has a substantially cylindrical proximal end member 32 of the bending-movement section 3 (hereinafter simply called the proximal end member 32) fixed on the distal end of the tube 21; bending joint pieces 33 connected to the proximal end member 32 and being capable of freely curving; and a distal end member 34 of the bending-movement section 3 (hereinafter simply called the distal end member 34). In the present embodiment, two bending joint pieces 33 in substantially the same size and shape are joined in the axial line direction. The number of the bending joint pieces 33 may be modified in consideration of a specific bending shape. In addition, a flexible layer 31 is provided to cover the outer surface extending from the proximal end member 32 to the distal end member 34. Preferably, the maximum outer diameter of the bending-movement section 3 should be set to ensure that the inner diameter of the lumenal tissue which is subjected to the insertion of the bending-movement section 3 is prevented from being expanded too significantly, and that the bending-movement section 3 can be inserted into lumens such as forceps channels formed in the endoscope used in combination with the endoscopic treatment instrument 1. More specifically and preferably, the outer diameter of the bending-movement section 3 according to the present embodiment should be up to 2.3 mm in view of the inner diameter of a bile duct which is subjected to the insertion of the bending-movement section 3.

Further referring to FIG. 2A, an angle wire 24 passed through the bending-movement section 3 has one of two ends attached to the distal end member 34, and the other end extending through the tube 21. In the bending-movement section 3, retracting the angle wire 24 in the axial line direction of the bending-movement section 3 allows the distal end member 34 to be retracted toward the proximal end member 32. The distal end member 34 upon being retracted causes the bending joint pieces 33 to move and curve, thereby allowing the bending-movement section 3 to bend.

Preferably, length L1 defined in the axial line direction of the bending-movement section 3 should be 5 to 12 mm between the distal end of the distal end member 34 and a section where the proximal end member 32 is connected to the most proximal bending joint piece 33. The preferable length of the bending-movement section 3 is set within the aforementioned range of length based on the shape of the lumenal tissue which is subjected to the insertion of the bending-movement section 3. In the present embodiment, the bending-movement section 3 set to have the length L1 is preferably applicable to a disease in which a relatively longer common duct exists between a duodenal papilla and a bile duct.

Figure 2B:
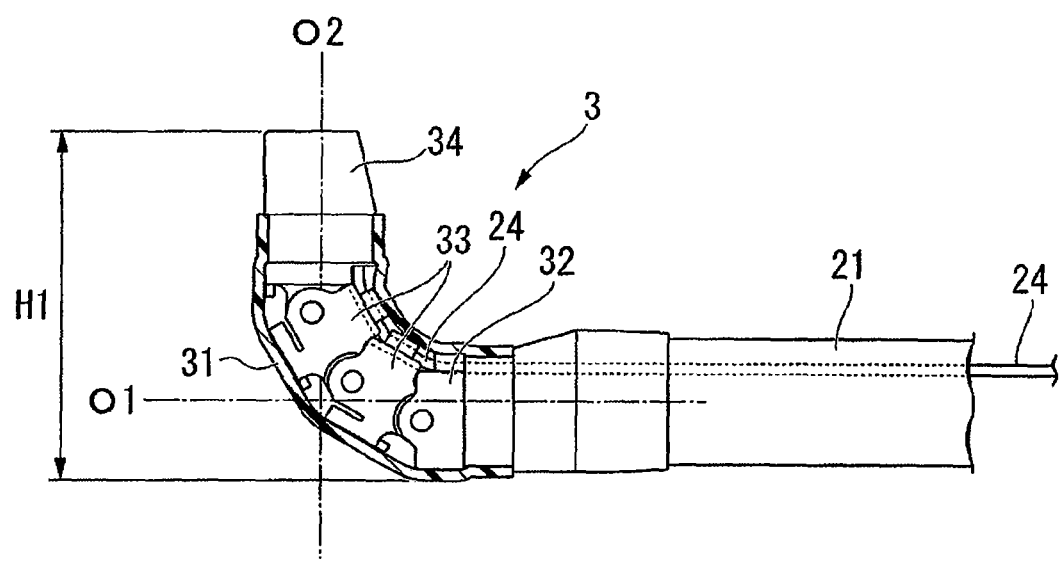
FIG. 2B is an enlarged view partially in cross section showing the distal end section of the treatment instrument that has been moved and bent.

FIG. 2B is an enlarged view partially in cross section showing a bending state of the bending-movement section 3. The bending-movement section 3 is capable of bending so that the direction of central axis line O2 of the distal end member 34 has substantially 90 degrees relative to the direction of central axis line O1 of the tube 21. Hereinafter, in the present specification, the bending direction in this manner will be defined as bending in the positive direction. In addition, the bending-movement section 3 is capable of bending on a plane including both the central axis lines O1 and O2. In FIG. 2B, reference symbol H1 indicates the maximum dilatable height of a lumen which is subjected to the insertion of the bending-movement section 3 and to the bending of the distal end of the distal end member 34 and the proximal end member 32. Preferably, the height H1 should be set between 2 mm and 8 mm. The height H1 is preset to be more significant than the inner diameter of the aforementioned common duct and to not exceed the maximum tolerable inner diameter of the common duct when an external force expands the common duct. That is, the height H1 is preset to allow the distal end and the proximal end of the bending-movement section 3, upon being bent, to reliably make contact with two opposing sites of an inner wall of the common duct.

Up to 8 mm of height H1 (the maximum dilatable height of a lumen) is preset in consideration that a dilation balloon for regular use in dilating a duodenal papilla in a commonly known Endoscopic Papillary Balloon Dilation (EPBD) has a dilatable diameter of 8 mm because this diameter can maintain functions of mamilla in the duodenal papilla. Therefore, possibilities can be reduced with respect to damage to the functions of mamilla in the duodenal papilla when the bending-movement section 3 of the endoscopic treatment instrument 1 according to the present embodiment inserted through the duodenal papilla into the common duct bends.

Figure 3A:
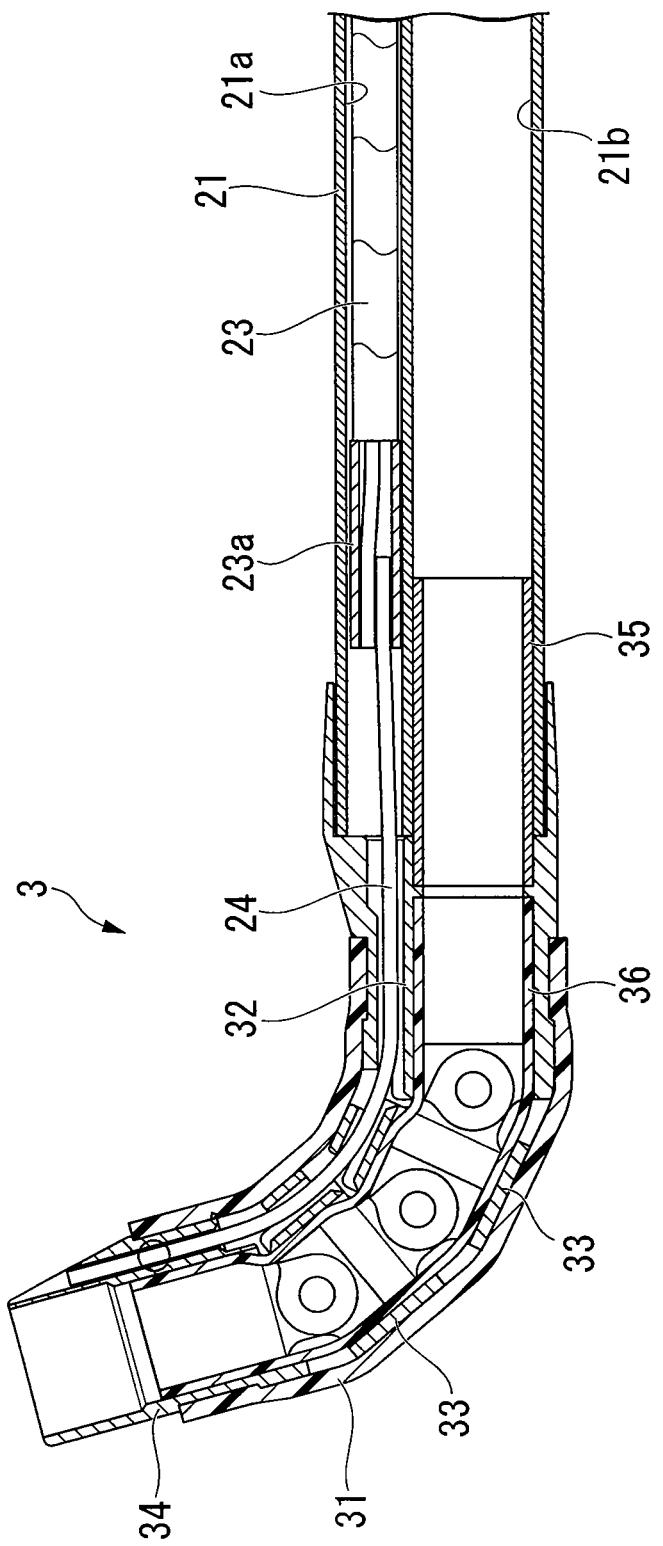
FIG. 3A is a cross sectional view showing a distal end of the treatment instrument that has been moved and bent.

FIG. 3A is an enlarged cross-sectional view showing the distal end of the endoscopic treatment instrument 1. The tube 21 has two lumens therethrough. A first lumen 21a has an operation wire 23 passing therethrough and connected to the angle wire 24 via a connection pipe 23a. In addition, a second lumen 21b has a coupling tube 35 inserted from the distal end of the second lumen 21b and fixed there. The second lumen 21b is tightly fixed to the proximal end member 32 via the coupling tube 35. In addition, the proximal end member 32, the bending joint pieces 33, and the distal end member 34 are assembled with each other to form a cylinder having a coaxial through hole having an aperture formed on the distal end of the distal end member 34. A flexible cylindrical flexible tube 36 is inserted into and fixed in this through hole to cover and seal gaps formed among the bending joint pieces 33 or the like. Preferably, the flexible tube 36 may include, for example, a fluorine compound for reducing sliding friction between an object passing through the flexible tube 36 and the flexible tube 36 while obtaining a sufficient space in the lumen.

Figure 3B:
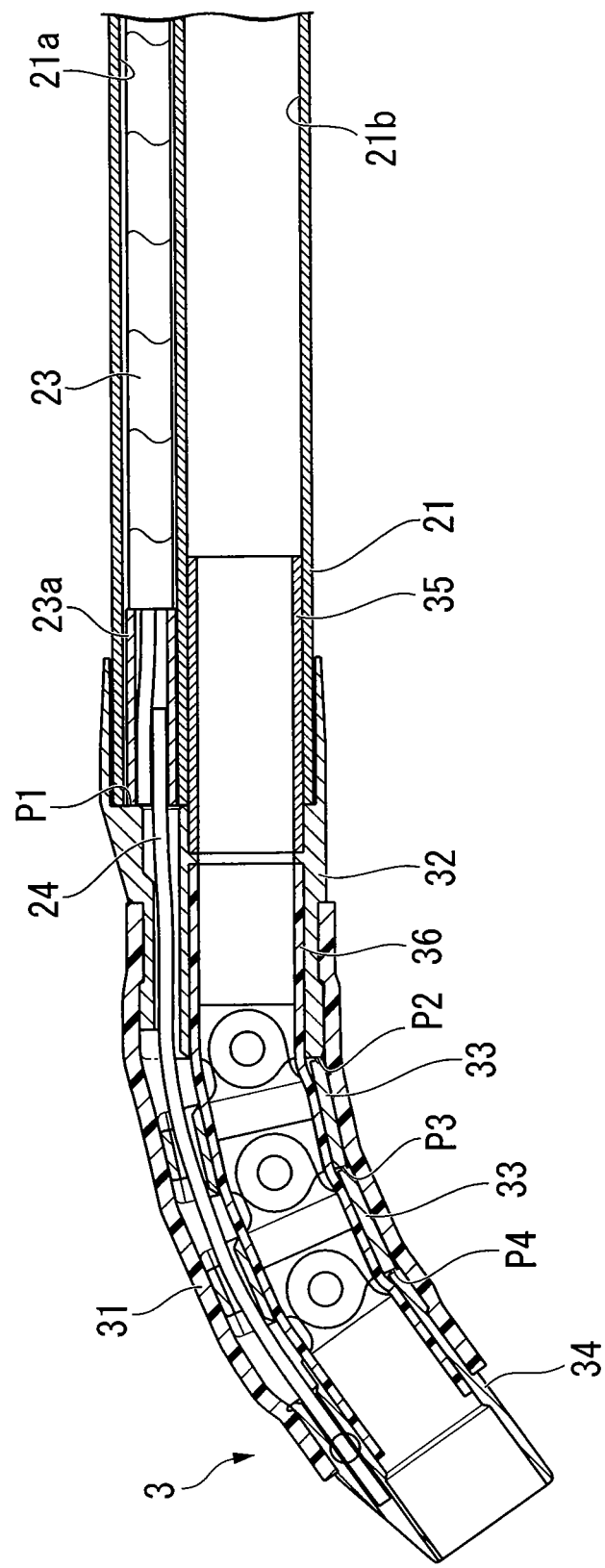
FIG. 3B is a cross sectional view showing the distal end of the treatment instrument that has been operated and extended.

FIG. 3B is a cross-sectional view showing the bending-movement section 3 when moved and extended from the bending state as shown in FIG. 3A. As shown in FIG. 3B, moving the operation wire 23 toward the bending-movement section 3 causes the connection pipe 23a to make contact with the proximal end member 32 at contact position P1. The bending joint pieces 33 in this state make contact with each other at contact positions P2, P3, and P4 and are supported there. In this mechanism, the wire operation wire 23 moving toward the bending-movement section 3 is limited in bending the bending-movement section 3. The bending-movement section 3 in this state is bent to a predetermined degree in the reverse direction to the aforementioned positive direction with respect to the central axis line of the bending-movement section 3. The predetermined degree to which the bending-movement section 3 bends in the reverse direction may be set arbitrarily based on the bending shape of the lumenal tissue which will be subjected to the insertion of the bending-movement section 3. Correlation will be explained later between the shape of the bending-movement section 3 in the reverse direction and the shape of the lumenal tissue.

Figure 4:
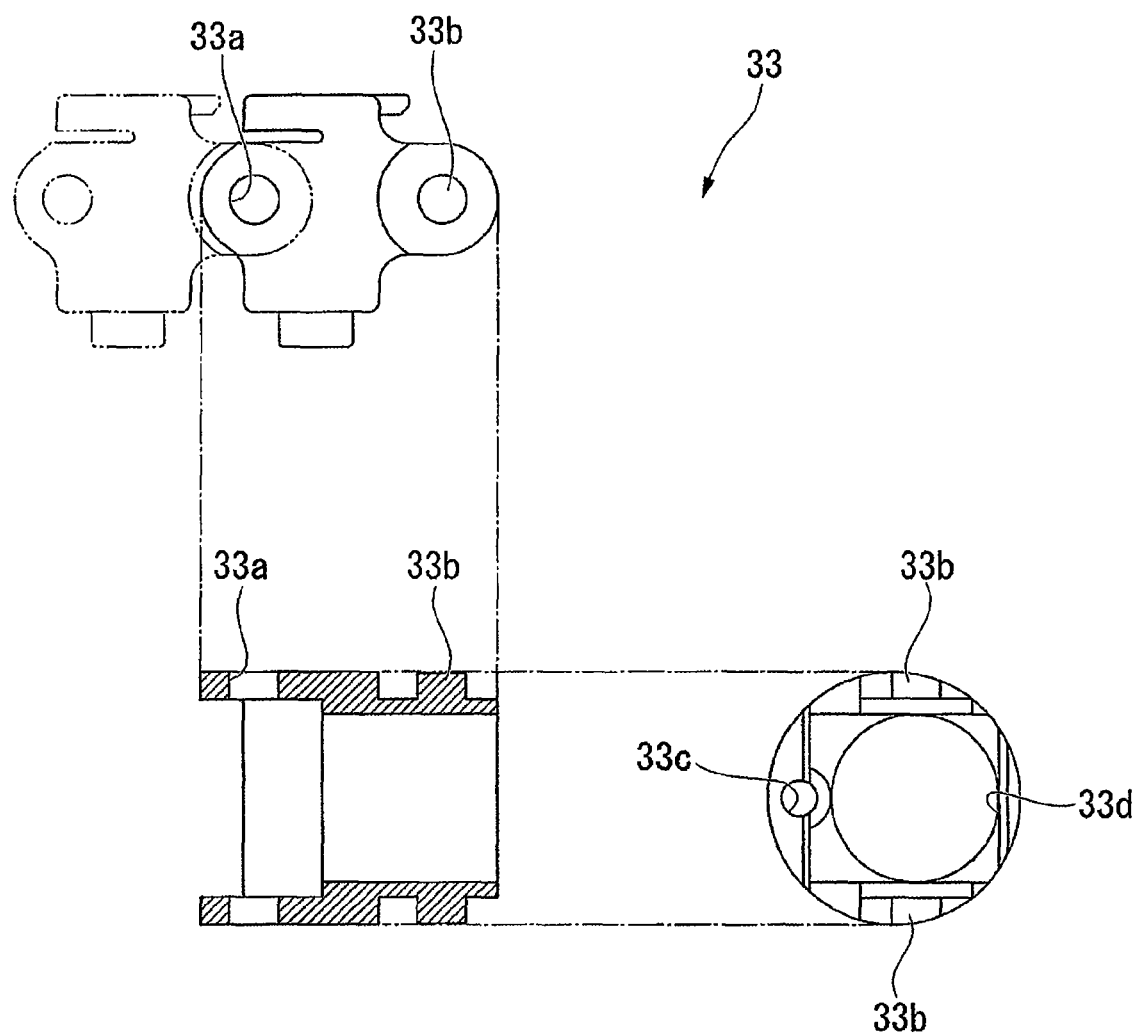
FIG. 4 shows components included in the bending section of the treatment instrument in orthographic views.

FIG. 4 shows the bending joint pieces 33 in orthographic views. As shown in FIG. 4, each bending joint piece 33 made from a flexible material has two holes 33a each of which will be subject to snap-fit with a projection 33 of an adjacent bending joint piece 33. Each projection 33b freely rotatable with respect to each hole 33a serves as a pivoting axis in the bending-movement section 3. In addition, a hole 33c formed in the axial line direction of each bending joint piece 33 allows the angle wire 24 to pass extendably or retractably therethrough. Furthermore, a hole 33d formed in the axial line direction of each bending joint piece 33 is capable of communicating with the second lumen 21b of the tube 21.

Figure 5:
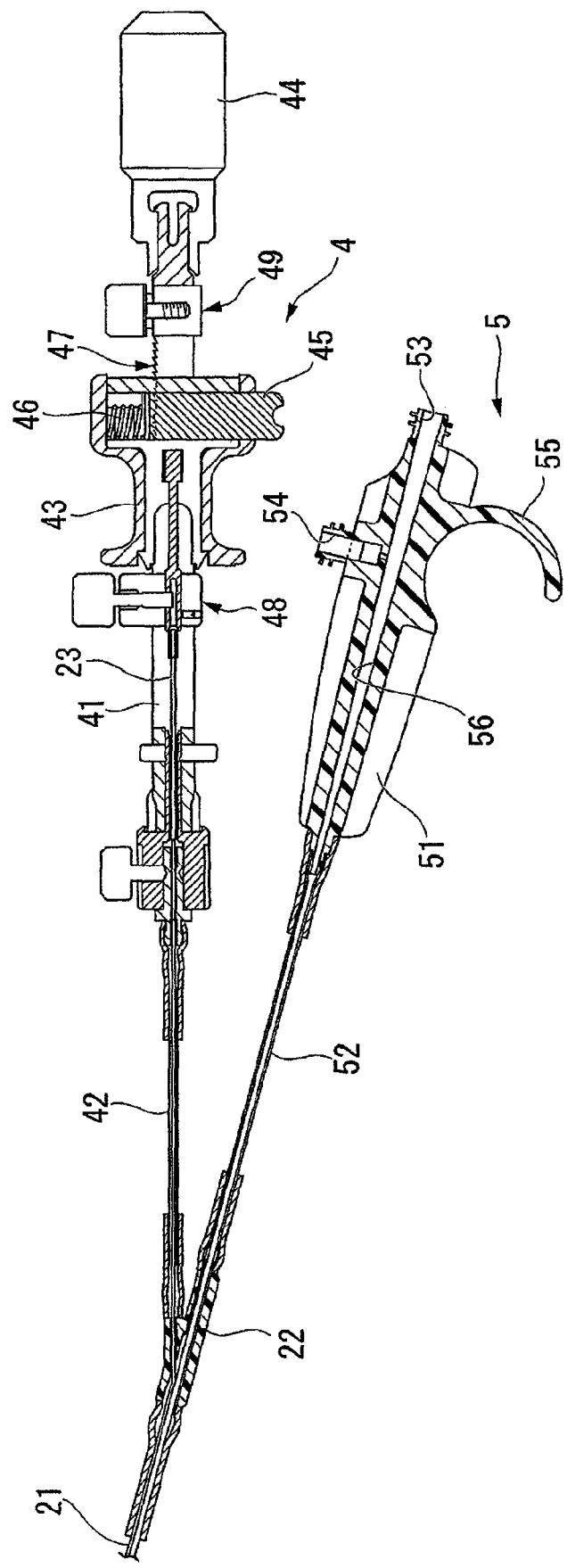
FIG. 5 is a partial cross sectional view showing an operating section of the configuration of the treatment instrument.

FIG. 5 is an enlarged view partially in cross section showing the first operating section 4 and the second operating section 5. The first lumen 21a (see FIG. 3A) formed in the tube 21 branches off in the connector 22 to the connection pipe 42. The operation wire 23 passing through the connection pipe 42 and a wire-fixing member 48 is fixed to the slider 43. The slider 43 has a push button 45 and a biasing member 46 which compresses the push button 45 toward the first operating unit 41. A ratchet section 47 having a plurality of indented corrugations is formed in a section where the push button 45 makes contact with an outer surface of the first operating unit 41. The ratchet section 47 upon engaging with the push button 45 at an arbitrary position in the axial line direction of the first operating unit 41 causes the slider 43 to be fixed there. Preferably, in this mechanism, the ratchet section 47 should not block the slider 43 moving toward the proximal end of the first operating unit 41 while the push button 45 must be operated for moving the slider 43 toward the distal end of the first operating unit 41. A stopper 49 provided on the first operating unit 41 is capable of making contact with the slider 43 and of limiting the movable range of the slider 43.

In the present embodiment, moving the slider 43 toward the proximal end of the first operating unit 41 causes the operation wire 23 fixed to the slider 43 to move toward the proximal end of the first operating unit 41, thereby retracting the distal end member 34 via the angle wire 24 fixed on the tip of the operation wire 23. Therefore, the bending-movement section 3 is bent in the positive direction. On the other hand, moving the slider 43 toward the distal end of the first operating unit 41 allows the bending-movement section 3 to be bent to the aforementioned predetermined degree in the reverse direction.

In addition, the connection pipe 52 communicates not only with the second lumen 21b of the tube 21 but also with the second operating unit 51. The second operating unit 51 has a hole 56 extending in the axial line direction and having two apertures of the first aperture 53 and the second aperture 54. The outer surfaces of the first aperture 53 and the second aperture 54 are connectable preferably to syringes or the likes having a commonly known leur lock mechanism.

Referring to FIGS. 6 to 18, operations and selective cannulation method using the endoscopic treatment instrument 1 of the present embodiment having the aforementioned mechanism according to the present invention will be explained as follows. In the following, examples will be explained according to a bile duct insertion method for inserting the endoscopic treatment instrument 1 selectively into the bile duct, and treatments carried out subsequently.

Figure 6:
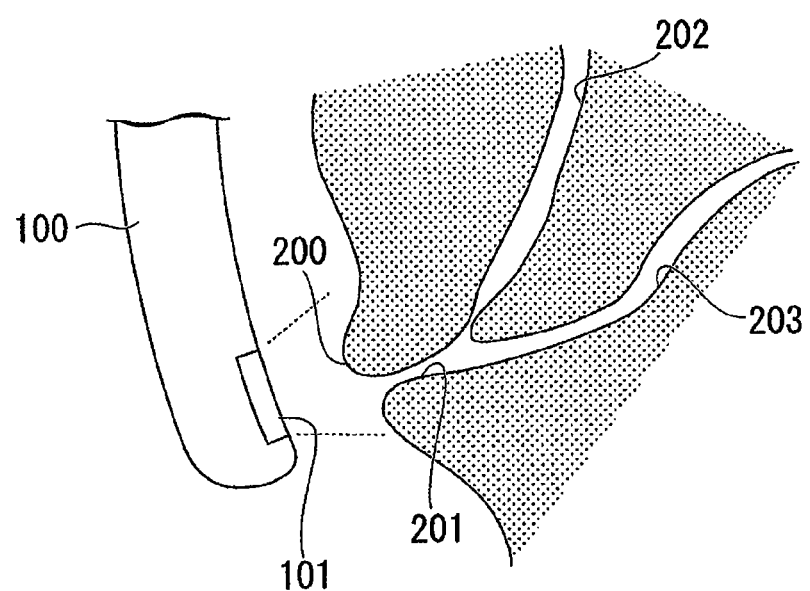
FIG. 6 is a schematic view showing a process of using the treatment instrument.

FIG. 6 is a schematic diagram showing the vicinity of the duodenal papilla. As shown in FIG. 6, a user inserts an endoscope 100 through a natural orifice of a patient into the body cavity. The endoscope 100 used in the present embodiment is of a side view type. The endoscope 100 is provided with a treatment section 101 for observing a treatment object or for projecting a treatment instrument. The user upon introducing the endoscope 100 to a duodenal papilla 200 captures the duodenal papilla 200 in the field view of the endoscope 100 (first step S1).

Figure 7A:
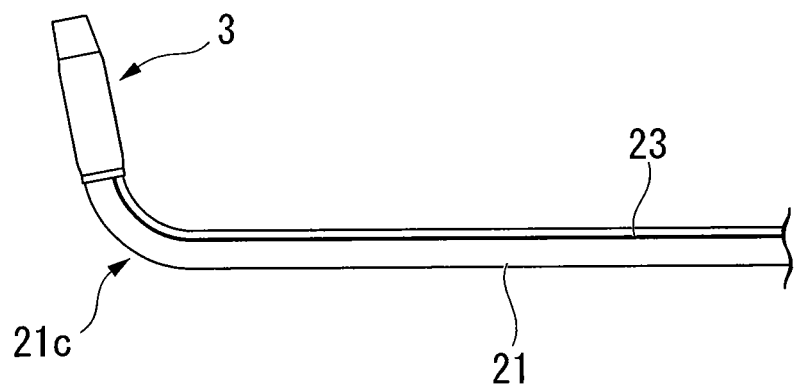
FIGS. 7A and 7B are schematic views showing a process of using the treatment instrument.
Figure 7B:
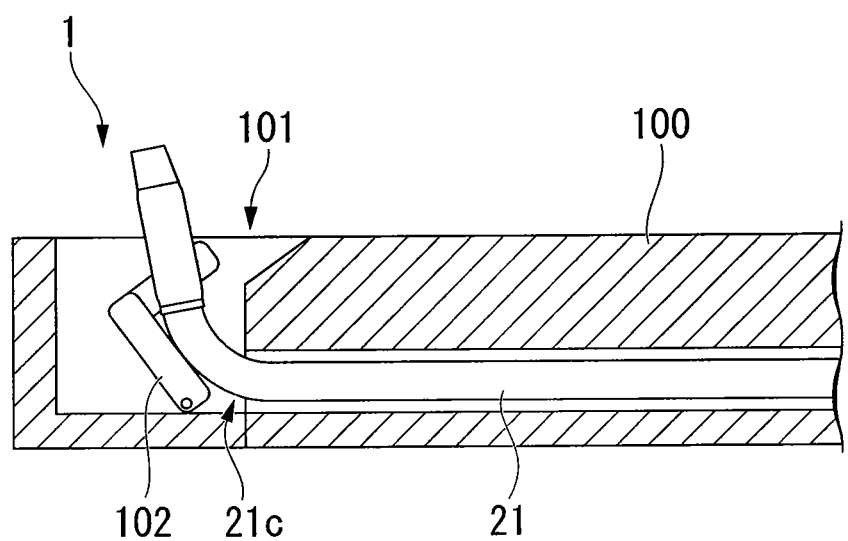
Figure 8:
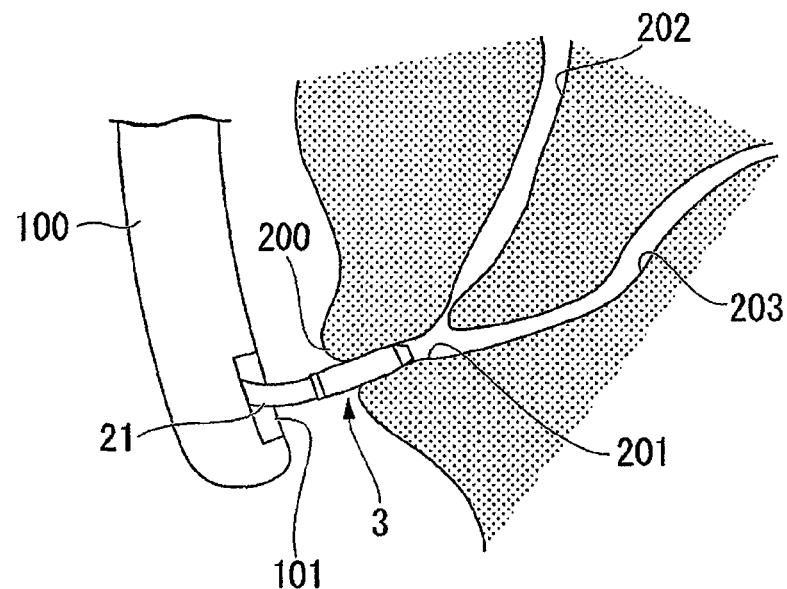
FIG. 8 is a schematic view showing a process of using the treatment instrument.

After that, the user inserts the endoscopic treatment instrument 1 into a commonly known forceps channel, which is not shown in the drawing, of the endoscope 100 toward the treatment section 101. FIG. 7A is a side view showing the distal end of the endoscopic treatment instrument 1. As shown in FIG. 7A, a part of the distal end of the tube 21 precurved to form a bending section 21c may be inserted into the forceps channel if necessary. FIG. 7B shows the endoscopic treatment instrument 1 placed in the endoscope 100. As shown in FIG. 7B, the endoscope 100 has a raising stand 102 provided therein for introducing the distal end of the endoscopic treatment instrument 1 from the treatment section 101 to the exterior thereof. The tube 21 having the aforementioned form of the bending section 21c and following the course defined along the raising stand 102 facilitates positioning of the endoscopic treatment instrument 1 in the rotational direction relative to the endoscope 100. The position of the endoscope 100 in the duodenum is determined in the first step S1 of the present embodiment using a predetermined manipulation in approaching duodenal papilla endoscopically. Since, in general, the endoscope 100 can be set to have a predetermined correlation in a position relative to the bile duct, making a precurve on the bending section 21c of the tube 21 is effective for regulating the rotational direction of the bending section 21c. Referring to FIG. 8, the bending-movement section 3 disposed on the distal end of the endoscopic treatment instrument 1 is projected from the treatment section 101 of the endoscope 100 and inserted through the aperture section of the duodenal papilla 200 (second step S2) into a lumenal tissue of common channel 201 (third step S3).

Figure 9:
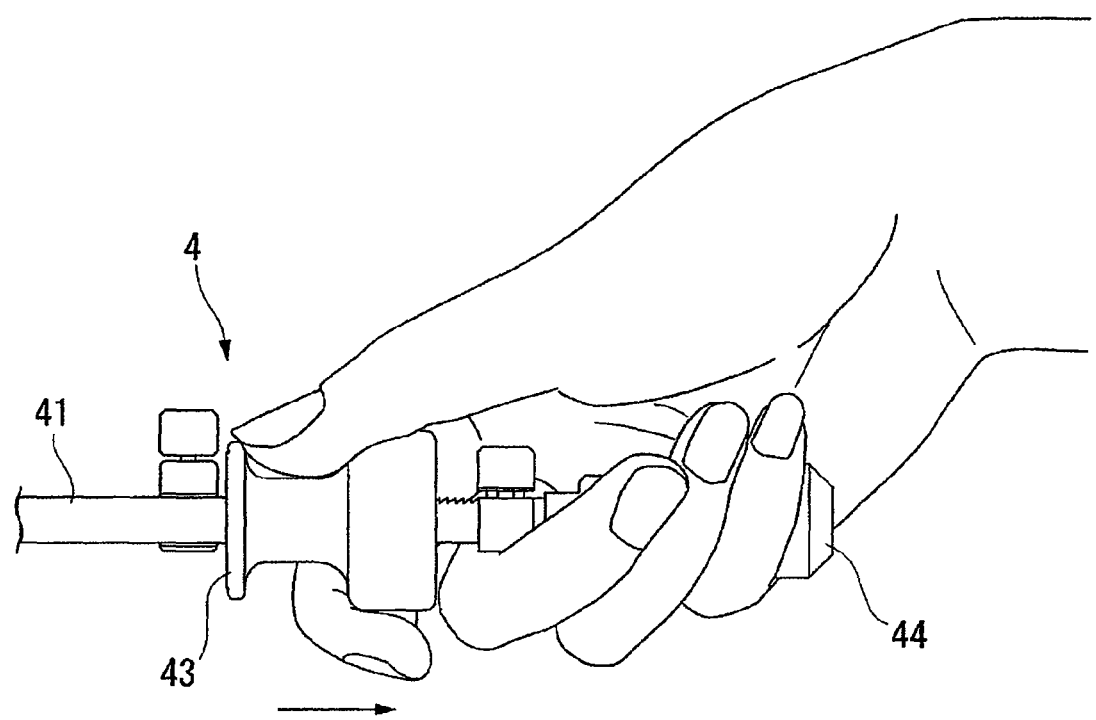
FIG. 9 is a schematic view showing a process of using the treatment instrument.
Figure 10:
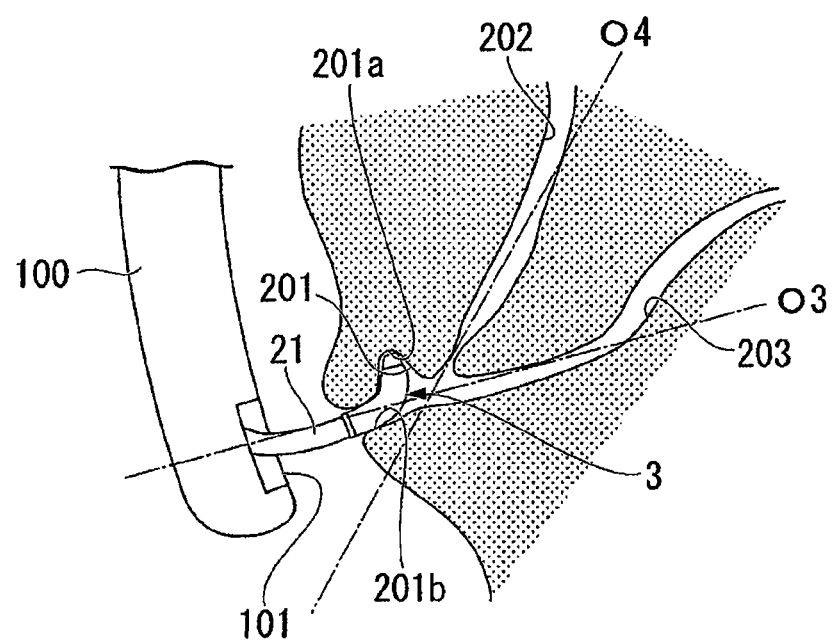
FIG. 10 is a schematic view showing a process of using the treatment instrument.

After that, the user retracts the slider 43 proximally while holding the grip 44 of the first operating section 4 as shown in FIG. 9. Then, as shown in FIG. 10, the bending-movement section 3 is bent, and the distal end thereof makes contact with the pipe wall of the common channel 201. The bending movement of the bending-movement section 3 is performed on the plane including the central axis lines O1 and O2 as shown in FIG. 2B. The direction of bending movement is defined along the plane including a central axis line O3 of the common duct 201 and a central axis line O4 of a bile duct 202. The distal end of the endoscopic treatment instrument 1 in this state makes contact with the inner wall surface of the common channel 201 at two points opposing in a radial direction (e.g., positions designated by reference symbols 201a and 201b) while the two points are included in the plane including the central axis lines O3 and 4 (fourth step S4). The inner wall of the common channel 201 supporting the distal end of the endoscopic treatment instrument 1 prevents the shaking of the tube 21 when pushed into the common channel 201. More specifically, shaking is prevented because the distal end of the distal end member 34 makes contact with the inner wall of the common channel 201 in the vicinity of the area of the bile duct 202; and because the outer surface of the flexible layer 31 at the section where the proximal end member is connected to the bending joint piece 33 makes contact with the area of the inner wall of the common channel 201 opposed to the bile duct 202 with reference to the central axis line O3 of the common channel 201.

Figure 11A:
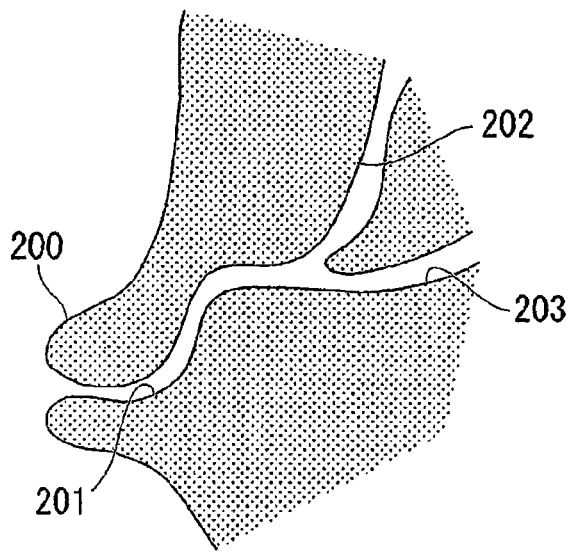
FIGS. 11A, 11B, and 11C are schematic views showing a process of using the treatment instrument.
Figure 11B:
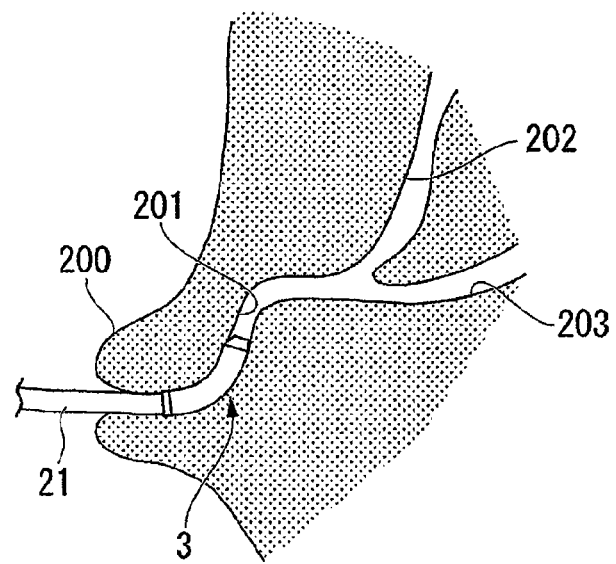
Figure 11C:
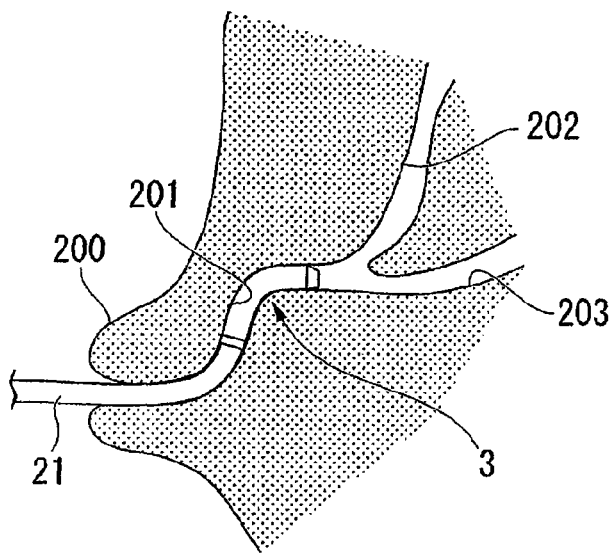

In some cases, the path formed between the duodenal papilla 200 and a branch section 204 may be crooked like the common channel 201 as shown in FIG. 11A. In this case, the distal end of the endoscopic treatment instrument 1 is guided to follow the shape of the common channel 201 and to pass through the crooked pipeway of the common channel 201 as shown in FIG. 11C while bending the bending-movement section 3 to an appropriate bending degree in the positive or reverse direction to follow the shape of the common channel 201 as shown in FIG. 11B. Extending or retracting the slider 43 relative to the first operating unit 41 while pushing the push button 45 provided on the slider 43 allows the bending-movement section 3 to make a desirable bending movement relative to the first operating unit 41.

Figure 12:
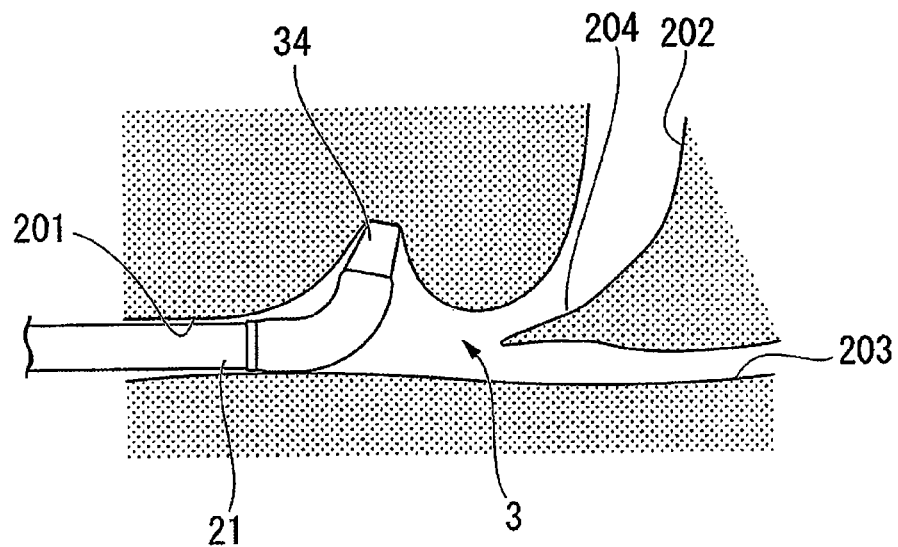
FIG. 12 is a schematic view showing a process of using the treatment instrument.

After that, the user pushes the tube 21 farther through the common channel 201 while maintaining the bending state of the bending-movement section 3 in the common channel 201 as shown in FIG. 12. Then, the distal end of the distal end member 34 of the endoscopic treatment instrument 1 is slid and moved farther into the common channel 201 while making contact with the inner wall of the common channel 201 (fourth step S4).

Figure 13:
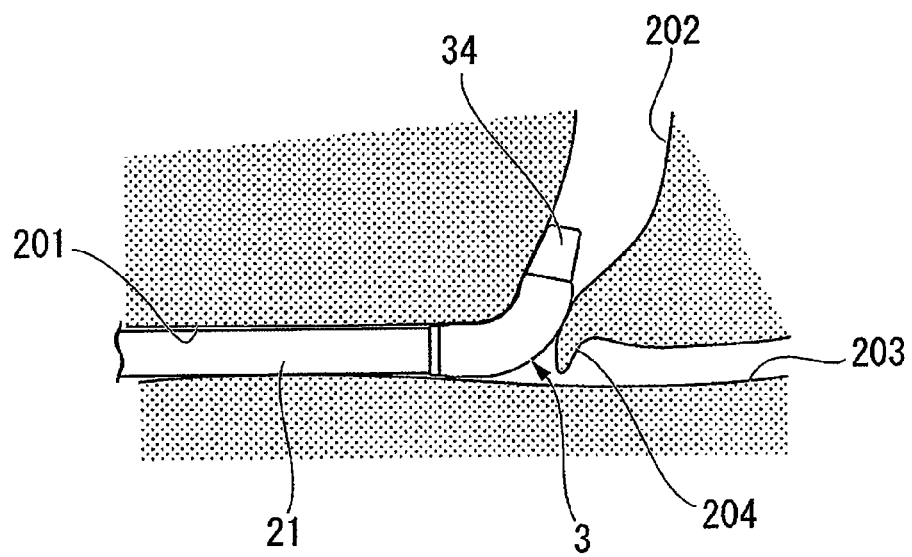
FIG. 13 is a schematic view showing a process of using the treatment instrument.

The common channel 201 is divided at the branch section 204 into the bile duct 202 and a pancreatic duct 203. As shown in FIG. 13, when the tube 21 is pushed farther into the common channel 201, the distal end member 34 upon reaching the branch section 204 is inserted from the branch section 204 into a predetermined branch lumen, i.e., the bile duct 202 (sixth step S6). In addition, the insertion of the distal end member 34 into the aperture of the bile duct 202 can be facilitated since the distal end of the distal end member 34 can deform or push aside the branch section 204 having ridges and grooves that block the aperture of the bile duct 202.

Pushing the tube 21 through the duodenal papilla 200 farther into the common channel 201 while bending the bending-movement section 3 in this way allows the bending-movement section 3 to be selectively inserted into the bile duct 202.

Figure 14:
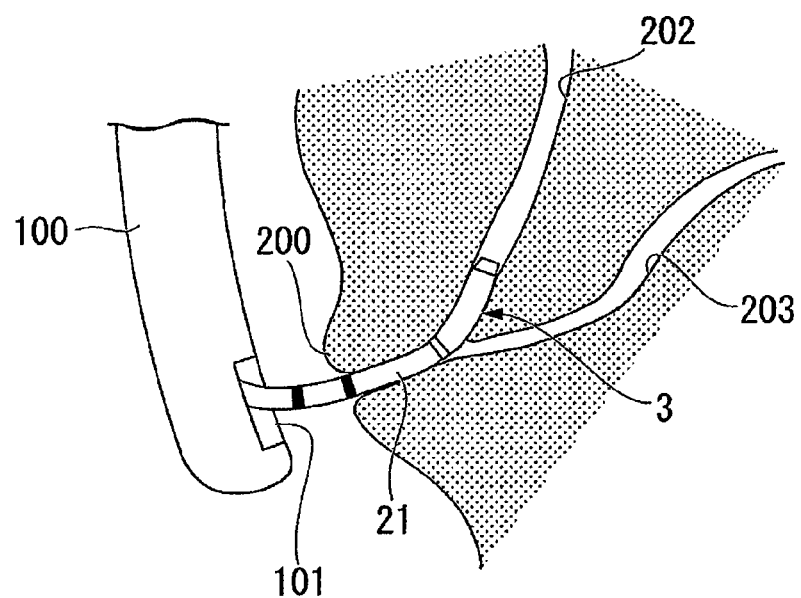
FIG. 14 is a schematic view showing a process of using the treatment instrument.

FIG. 14 is a schematic view showing the bile duct 202 having undergone the selective cannulation successfully. The user carries out a predetermined treatment to the bile duct 202 in this state. For example, a contrast agent is injected by using the second operating section 5 shown in FIG. 5 into the first aperture 53 or the second aperture 54 through the hole 56 into the second lumen 21b of the tube 21, and then the contrast agent is discharged from the distal end of the bending-movement section 3 for capturing contrast radiographic images of the bile duct 202.

Figure 15:
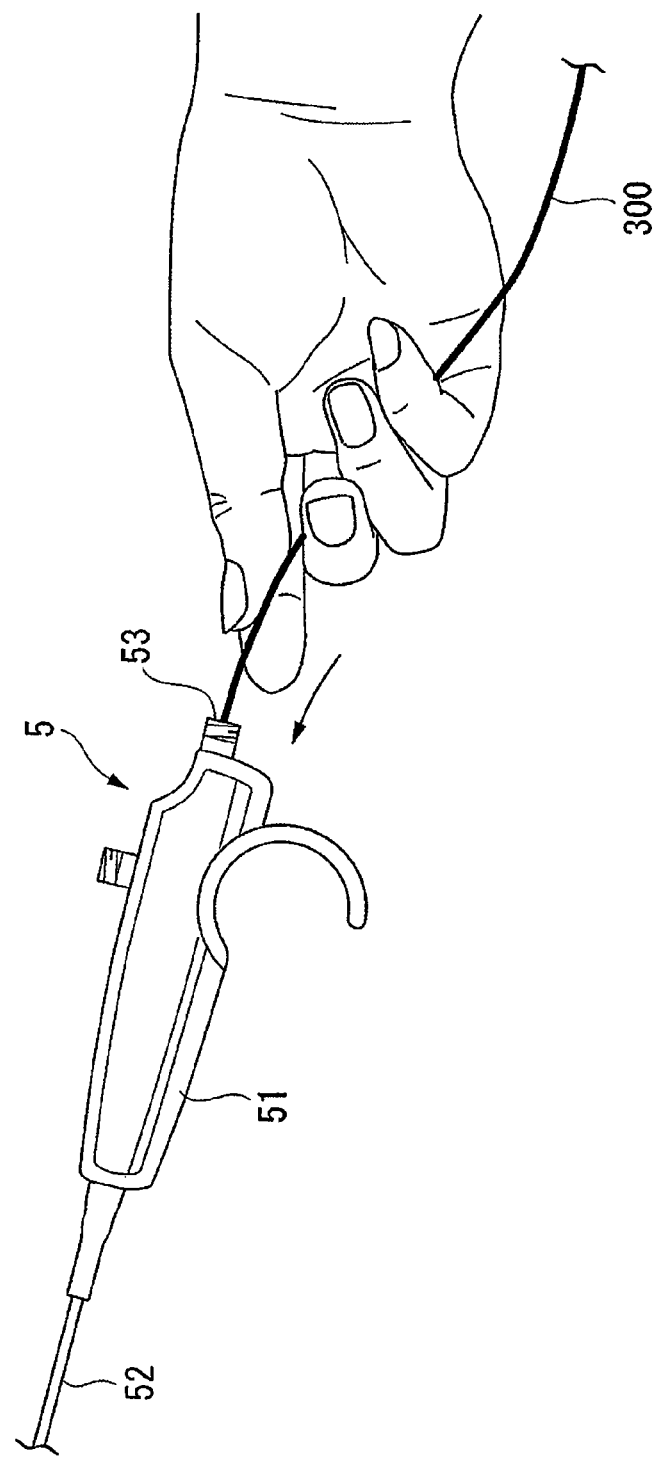
FIG. 15 is a schematic view showing a process of using the treatment instrument.

Alternatively, a flexible guidewire 300 may be inserted into the first aperture 53 of the second operating section 5 as shown in FIG. 15. The guidewire 300 will meet reduced resistance during the insertion through the tube 21 since the connection pipe 52 is aligned in the axial line direction of the tube 21 as shown in FIG. 1. This results in the user being able to insert the guidewire 300, and tactile sense perceived when inserting the guidewire 300 into the body cavity can be conveyed to and perceived by the user.

Figure 16:
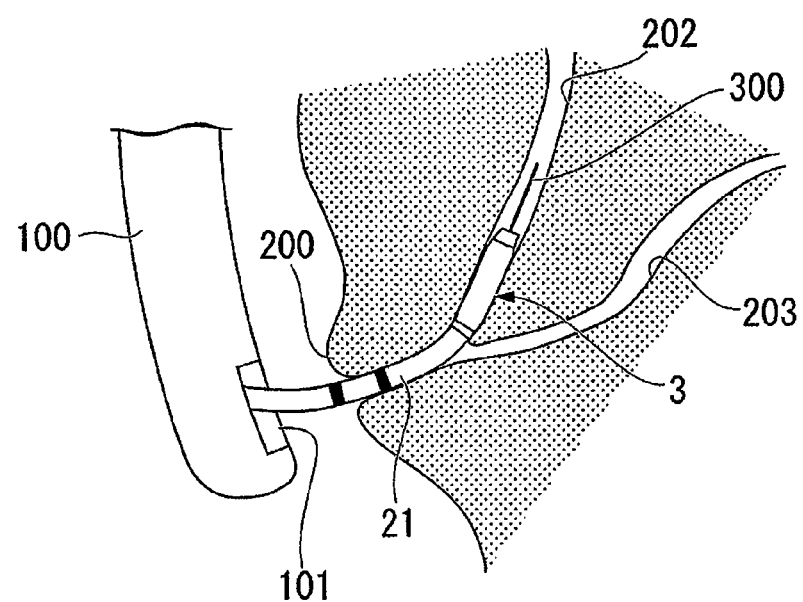
FIG. 16 is a schematic view showing a process of using the treatment instrument.
Figure 17:
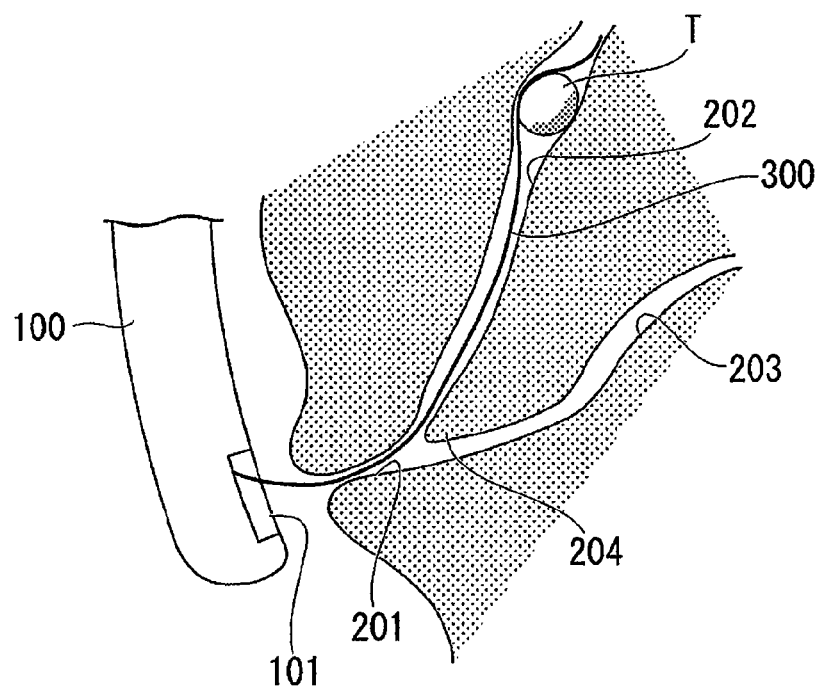
FIG. 17 is a schematic view showing the treatment instrument that has been used for treatment.

As shown in FIG. 16, the user projects the guidewire 300 from the distal end of the bending-movement section 3 and inserts the guidewire 300 through the bile duct 202. For example, if a foreign matter T exists in the bile duct 202 as shown in FIG. 17, the guidewire 300 is introduced across the foreign matter T, and then the endoscopic treatment instrument 1 is removed from the endoscope 100 while maintaining the guidewire 300 there.

Figure 18:
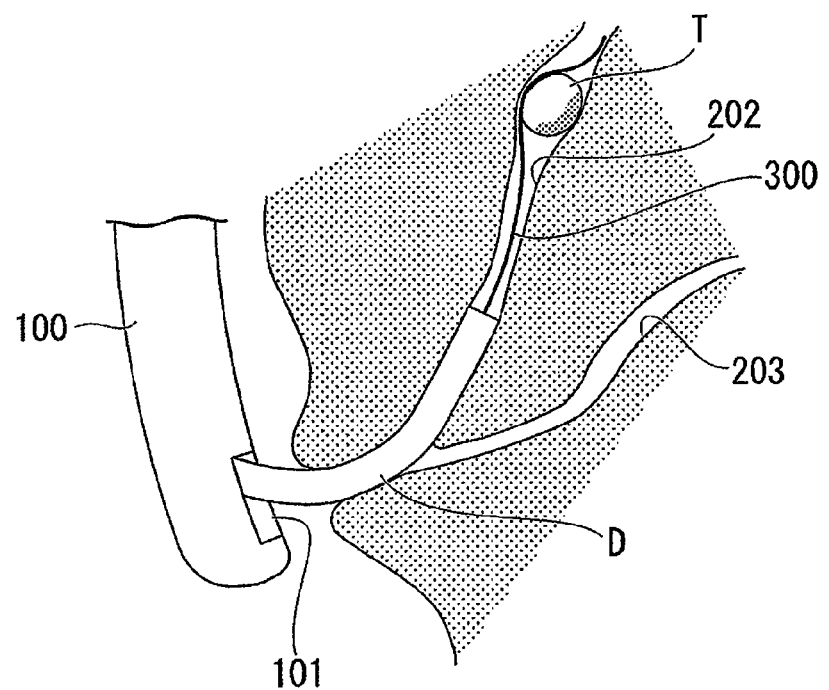
FIG. 18 is a schematic view showing the treatment instrument that has been used for treatment.

Subsequently, an appropriate treatment instrument D is introduced along the guidewire 300 as shown in FIG. 18 to conduct a predetermined operation to the foreign matter T.

Although the distal end of a treatment instrument of a conventional endoscopic treatment instrument was capable of bending and moving, the distal end of the treatment instrument could not be supported at the inner wall of a lumenal tissue such as the aforementioned common duct or the like; therefore, the treatment instrument must have been pushed while continuing to push a point of the distal end of the treatment instrument onto the inner wall of the lumenal tissue. Therefore, it was difficult to insert the endoscopic treatment instrument into the common duct while maintaining the upper wall of the common duct in a raised condition like the aforementioned method using the endoscopic treatment instrument 1 according to the present embodiment. Sometimes, the position of the treatment instrument deviated from a predetermined position in the lumenal tissue because of shaking of the user's hand.

Another problem was that insertion of the treatment instrument into the bile duct having an unidentified path required a high degree of skill.

In another case, sometimes, a bending part deflects from the duodenal papilla when the distal end of the treatment instrument is inserted into, the duodenal papilla through the common duct when, for example, the length of a bending part in the axial line direction is inappropriate. In this case, it was difficult for the user to control the distal end of the treatment instrument and to insert it into the bile duct while tracing the upper wall of the common duct because a supporting point for the bending part is absent in the common duct.

Furthermore, the endoscope and the treatment instrument must have been bent and moved cooperatively because bending the distal end of the treatment instrument caused the bending part deflected from the duodenal papilla to bend and move accordingly; therefore, the cooperative movements for the endoscope and the treatment instrument needs a skill. This was a problem because the aforementioned circumstance was a factor of a lowered success rate for the selective cannulation associated with the bile duct.

In another case, if the distal end of a conventional catheter had less significant stiffness than tissue sclerosis such as a malignant tumor, the distal end of the catheter could not be aligned in the user's intended direction.

According to the endoscopic treatment instrument 1 and the selective cannulation method in the present embodiment, the bending-movement section 3 disposed on the distal end of the endoscopic treatment instrument 1 is bent while making contact with the inner surface of the lumenal tissue common channel 201, and the distal end member 34 that is the distal end of the bending-movement section 3 is supported in the lumenal tissue while being directed toward the bile duct 202 which will be subjected to the selective cannulation.

Therefore, the user can insert the distal end member 34 into the bile duct 202 easily without using a high degree of skill for disposing the distal end of the treatment instrument along the pipe wall of the common channel 201 that has been required for the conventional treatment instrument.

Figure 19:
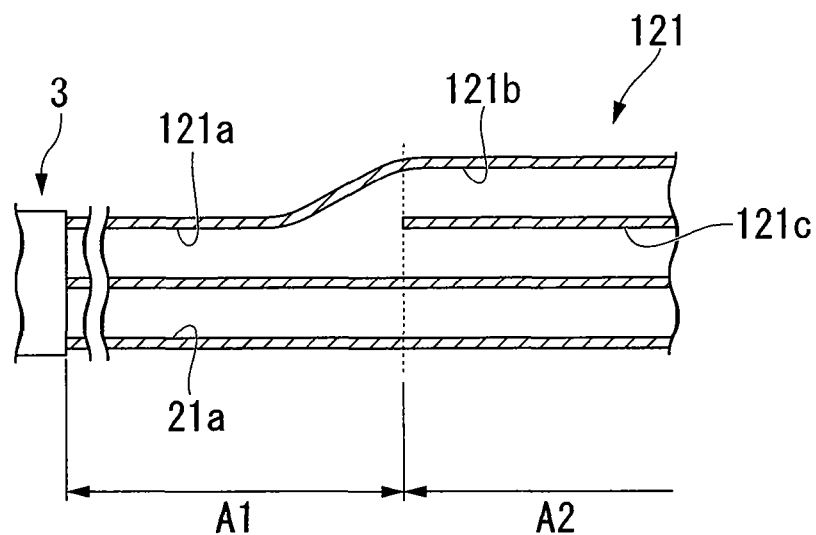
FIG. 19 is a schematic view showing a modified example of a tube used in the treatment instrument.

It should be noted that the aforementioned embodiment may adopt a tube 121 as schematically shown in FIG. 19 in place of the tube 21. The tube 121 is a multi-lumen tube having a first area A1 in the vicinity of the bending-movement section 3 including two lumens 121a and 21a; and a second area A2 having a first branch lumen 121b divided from the lumen 121a, and a second branch lumen 121c. The first branch lumen 121b is a lumen for flowing contrast agent, and the second branch lumen 121c is a lumen for inserting the guidewire 300 therethrough. The tube 121 having a more reduced diameter of the first area A1 than that of the second area A2 provides a reduced diameter of the distal end of the endoscopic treatment instrument 1, thereby reducing the load to the lumenal tissue applied when inserting the tube 121 into the common channel 201 or the bile duct 202. In addition, the tube 121 having two independent lumens, i.e., the first branch lumen 121b for flowing the contrast agent therethrough and the second branch lumen 121c for passing the guidewire 300 therethrough allows resistance conveyed to the user's hand to be reduced when injecting the contrast agent. It should be noted that, preferably, the length of the first area A1 in the axial line direction should be more significant than the distance between the duodenal papilla 200 and the bile duct 202, i.e., about 200 mm in the present embodiment.

Figure 20:
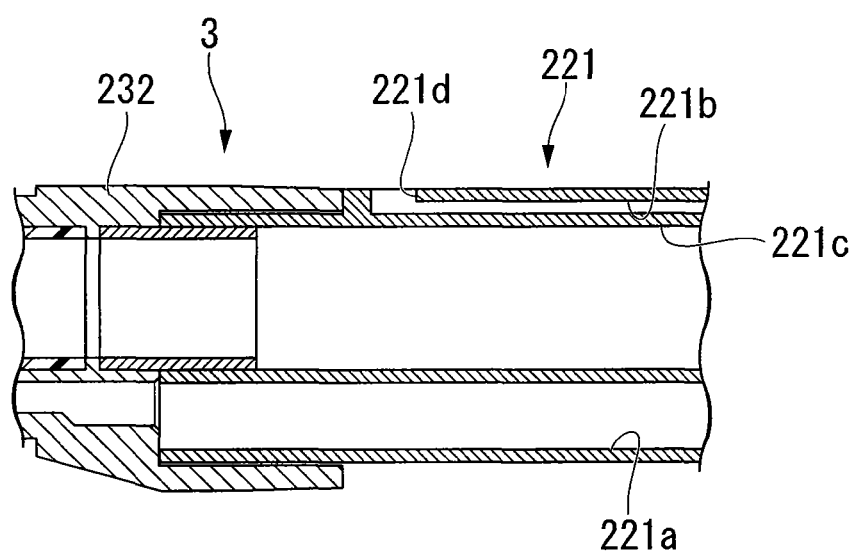
FIG. 20 is a schematic view showing another modified example of the tube used in the treatment instrument.

Alternatively, a tube 221, in place of the tube 21, as schematically shown in FIG. 20 may be adopted that has an operation wire lumen 221a, a contrast agent lumen 221b, and a guidewire lumen 221c that are formed separately therein. In this configuration, the contrast agent lumen 221b in this state has a side aperture 221d disposed on a lateral side of the tube 221 for ejecting the contrast agent from the side aperture 221d. In addition, in place of the proximal end member 32 of the bending-movement section 3, the aforementioned embodiment has a proximal end member 232 of the bending-movement section (hereinafter simply called the proximal end member 232) which can be connected to the tube 221 preferably. The proximal end member 232 is fixed to the tube 221 and has a correlation so as to not block the side aperture 221d.

This configuration adopting the tube 221 for ejecting the contrast agent through the contrast agent lumen 221b from the side aperture 221d can eliminate a pipeway used for flowing the contrast agent to the distal end through the bending-movement section 3. This configuration has the effect of supplying the contrast agent into the lumenal tissue while reducing resistance accompanying when injecting the contrast agent into the lumenal tissue when the maximum inner diameter of the bending-movement section 3 is so limited based on the inner diameter of the lumenal tissue which will be subjected to the insertion of the bending-movement section 3 that a sufficient inner diameter of the lumen cannot be obtained for flowing the contrast agent thereinside.

Figure 21:
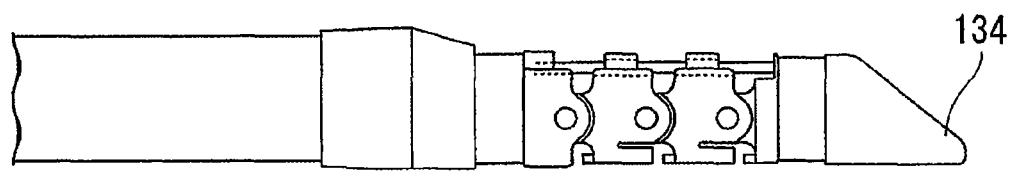
FIG. 21 is a side view showing the modified example of the bending-movement section used in the treatment instrument.

Alternatively, this configuration may be provided with a distal end member 134 of the bending-movement section (hereinafter simply called the distal end member 134) having a more oblique distal end as shown in FIG. 21 in place of the distal end member 34. The distal end member 134 in this shape capable of squeezing into the constricted entrance of a predetermined branch lumen in the branch section of the lumenal tissue can achieve a high success rate of selective cannulation.

Figure 22:
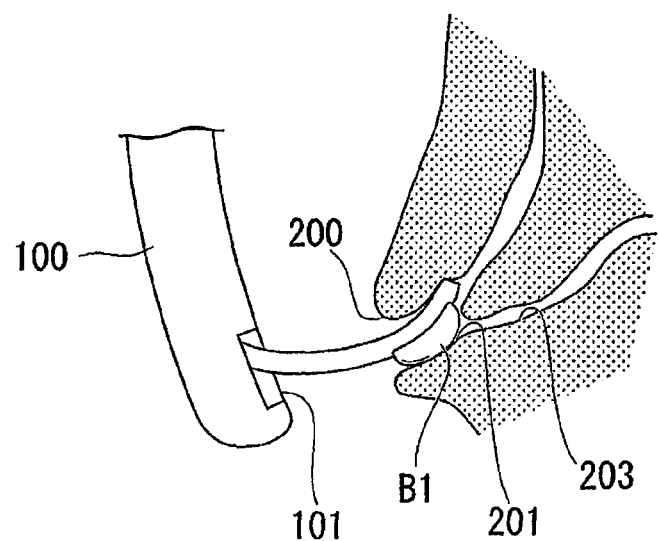
FIG. 22 is a schematic view showing another modified example of the bending-movement section used in the treatment instrument.

It should be noted that the selective cannulation method explained in the present embodiment is desirably applicable not only to the endoscopic treatment instrument 1 of the present embodiment but also to an endoscopic treatment instrument having another configuration capable of deforming or bending the distal end. For example, in an adoptable configuration, a turning axis is provided in a section located 5 to 12 mm from the distal end of the endoscopic treatment instrument to bend the distal end of the endoscopic treatment instrument instead of eliminating a plurality of bending joint pieces 33 provided in the endoscopic treatment instrument 1 of the present embodiment. The effect equivalent to that of the present embodiment can be achieved in another adoptable configuration having a deformable balloon capable of dilating in the radial direction of the tube 21 provided on the outer surface of the distal end of the endoscopic treatment instrument while the distal end of the endoscopic treatment instrument makes contact with two opposing points of the inner surface of the common duct. For this configuration, a balloon B 1, as shown in FIG. 22, inflatable outward in the radial direction of the tube 21 from a point of an outer circumferential surface of the distal end of the tube 21 may be adopted.

Figure 23:
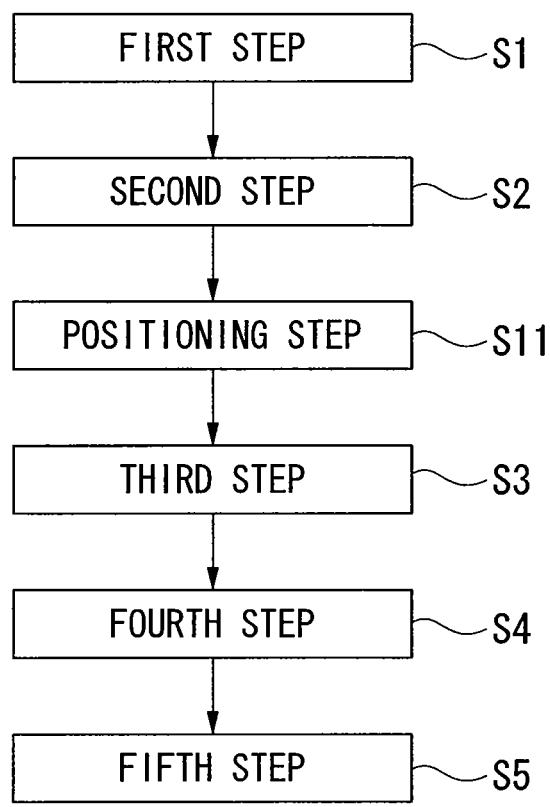
FIG. 23 is a flowchart showing a selective cannulation method according to a second embodiment of the present invention.

Referring now to FIG. 23, a second embodiment of the present invention will be explained. It should be noted that configurations that are similar to those of the previously explained first embodiment will be assigned the same numeric symbols and redundant explanations thereof will be omitted. FIG. 23 is a flowchart showing the selective cannulation method according to the present embodiment.

The present embodiment includes a positioning step S11 for rotating the insertion section 2 of the endoscopic treatment instrument 1 around the axial line after the third step S3 having inserted the endoscopic treatment instrument 1 through the common channel 201; and for aligning the bending direction of the distal end of the endoscopic treatment instrument with the direction to which the aperture of the endoscopic treatment instrument is directed.

The positioning step S11 may be performed prior or subsequent to bending of the bending-movement section 3 as long as the positioning step S11 is performed prior to inserting the distal end member 34 into the bile duct 202. That is, the positioning step S11 should be performed at least once at any position subsequent to the second step S2 and prior to the fifth step S5. The present embodiment capable of accurate micro-adjustment for the direction of the distal end of the endoscopic treatment instrument 1 toward the aperture section of the bile duct readily increases the success rate for the selective cannulation into the lumenal tissue such as a bile duct. In addition, the direction of the distal end member 34 can be changed without damaging the common duct after bending the bending-movement section 3 since the height H1 of the bending-movement section 3 upon being bent, as explained in the aforementioned first embodiment, indicates the maximum height for expanding the common duct is less significant than the inner diameter of the most expanded case of the common channel 201.

Although the present invention has been described with respect to its preferred embodiments, the present invention is not limited to the embodiments described above. The configuration of the present invention allows for addition, omission, substitution and further modification without departing from the spirit and scope of the present invention.

For example, an image-capturing mechanism capable of capturing the image of an object within the lumenal tissue may be provided in or on the insertion section 2 of the endoscopic treatment instrument 1. For example, in an adoptable configuration, the image-capturing mechanism of a built-in type may be included in the distal end member 34 provided on the distal end of the bending-movement section 3 provided on the distal end of the insertion section 2. Another adoptable configuration for the image-capturing mechanism may include a solid-state image-capturing mechanism having a CCD or CMOS area-imaging sensor, or a fiber scope mechanism extending from the distal end member 34 to the proximal end handled by the user.

The present invention is not limited to the above descriptions but is limited only by the appended claims.

What is claimed is:
1. A selective cannulation method for a luminal tissue's branch section, the method comprising:
 a first step of guiding an endoscope having a forceps channel to an aperture section of the luminal tissue which has the branch section for a bile duct and a pancreatic duct;

a second step of inserting a distal end of an endoscopic treatment instrument through the forceps channel into a common channel via the aperture section;

a third step of positioning an actively bendable distal section of the endoscope treatment instrument between the aperture section and the branch section;

a fourth step of bending the distal end of the endoscopic treatment instrument toward the bile duct in the common channel so that a proximal end of the actively bendable distal section of the endoscope treatment instrument is placed in the common channel, and making contact therewith of the bile duct side of the common channel before the distal end of the endoscopic treatment instrument reaches the branch section;

a fifth step of sliding and moving the distal end of the endoscopic treatment instrument to the branch section while maintaining the actively bendable distal section of the endoscopic treatment instrument in a bending state and a contacting state with the bile duct side of the common channel; and a sixth step of inserting the distal end of the endoscopic treatment instrument under the bending state into the bile duct divided from the branch section.

2. The selective cannulation method according to claim 1, further comprising:

a positioning step performed subsequent to the second step and prior to the fifth step, the positioning step including:

rotating and moving the endoscopic treatment instrument around an axial line; and positioning a rotational position of the endoscopic treatment instrument so that the distal end of the endoscopic treatment instrument is directed to the aperture of the branch lumen.

3. The selective cannulation method according to claim 1, further comprising:

a step of disposing a guide wire, for guiding another treatment instrument through the endoscopic treatment instrument; and a removal step for removing the endoscopic treatment instrument while indwelling the guide wire after the guide wire has been disposed at a predetermined position.

4. The selective cannulation method according to claim 3, further comprising:

a step of guiding another treatment instrument along the guide wire after the removal step.

5. The selective cannulation method according to claim 1, wherein the fourth step comprises that the distal end of the endoscopic treatment instrument, in the bending state, makes contact with the bile duct side of the common channel, and an outer surface, with respect to the bending state, in an outer periphery of the endoscopic treatment instrument makes contact with an opposite to the bile duct side of the common channel.

6. The selective cannulatio method according to claim 1, wherein:

the fourth step comprises fixing the actively bendable distal section in the bending state, and fixing a bending direction of the actively bendable distal section in the common channel, and the fifth step comprises sliding and moving the distal section of the endoscopic instrument while maintaining the bending state and fixing the bending direction.

* * * * *